US008426462B2

(12) United States Patent
Jaouen et al.

(10) Patent No.: US 8,426,462 B2
(45) Date of Patent: Apr. 23, 2013

(54) FERROCENE DERIVATIVES WITH ANTICANCER ACTIVITY

(75) Inventors: Gérard Jaouen, Cachan (FR); Anne Vessieres-Jaouen, Cachan (FR); Damian Plazuk, Garbatma Letnisko (PL)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 13/002,177

(22) PCT Filed: Jul. 2, 2009

(86) PCT No.: PCT/EP2009/058309
§ 371 (c)(1),
(2), (4) Date: Mar. 18, 2011

(87) PCT Pub. No.: WO2010/000793
PCT Pub. Date: Jan. 7, 2010

(65) Prior Publication Data
US 2011/0190391 A1    Aug. 4, 2011

(30) Foreign Application Priority Data
Jul. 3, 2008  (FR) ..................... 08 54533

(51) Int. Cl.
*A01N 55/02* (2006.01)
*A61K 31/295* (2006.01)
(52) U.S. Cl.
USPC .......................................... 514/502; 556/144
(58) Field of Classification Search .................. None
See application file for complete search history.

(56) References Cited

U.S. PATENT DOCUMENTS 5,496,846 A * 3/1996 Wilson et al. ................. 514/449
2004/0175415 A1* 9/2004 Chan et al. .................... 424/449

OTHER PUBLICATIONS

International Search Report issued in application No. PCT/EP2009/058309 on Sep. 21, 2009.
Hillard et al., "Organometallic diphenols: The importance of organometallic moiety on the expression of a cytotoxic effect on breast cancer cells," Journal of Organometallic Chemistry, vol. 692, pp. 1315-1326, 2007.
Abeysinghe et al., "Antitumour bis(cycolpentadienyl) metal complexes: titanocene and molybdocene dichloride and derivatives," Dalton Trans., pp. 3474-3482, 2007.
Hillard et al., "The influence of phenolic hydroxyl substitution on the electron transfer and anti-cancer properties of compounds based on the 2-ferrocenyl-1-phenyl-but-1-ene motif," Dalton Trans., pp. 5073-5081, 2007.
Rosenberg et al., "Plantinum Compounds: a New Class of Potent Antitumour Agents," Nature, vol. 222, pp. 385-386, Apr. 26, 1969.
Rosenberg et al., "Inhibition of Cell Division in *Escherichia coli* by Electrolyis Products from a Platinum Electrode," Nature, vol. 205, pp. 698-699, Feb. 13, 1965.
Wong et al., "Current Status of Platinum-Based Antitumour Drugs," Chem. Rev., vol. 99, pp. 2451-2466, 1999.
Nakayama et al., "1,1,2,2-Tetrakis(2-tripycyl)ethylene," J. Chem. Soc., pp. 974-975, 1986.
Rinehart et al., "Organic Chemistry of Ferrocene. V. Cyclization of ω-Ferrocenylaliphatic Acids," J. Am. Chem. Soc., vol. 84, No. 17, pp. 3263-3269, 1962.
Almássy et al., "[5]Ferrocenophane based ligands for stereoselective Rh-catalyzed hydrogenation and Cu-catalyzed Michael addition," Tetrahedron: Asymmetry, vol. 18, pp. 1893-1898, 2007.
Hillard et al., "A Series of Unconjugated Ferrocenyl Phenols: Prospects as Anticancer Agents," ChemMedChem, vol. 1, pp. 551-559, 2006.
Vessières et al., "Metal complex SERMs (selective oestrogen receptor modulators). The influence of different metal units on breast cancer cell antiproliferative effects," Dalton Trans., pp. 529-541, 2006.
Jaouen et al., "Organometallics Targeted to Specific Biological Sites: the Development of New Therapies," Bioorganometallics, Chapter 3, pp. 65-95, 2005.
Wang et al., "Reactions of a Ruthenium(II) Arene Antitumor Complex with Cysteine and Methionine," Inorganic Chemistry, vol. 41, pp. 4509-4523, 2002.
Allardyce et al., "[Ru(n$^6$-p-cymene)Cl$_2$(pta)] (pta= 1,3,5-triaza-7phosphatiricyclo-[3.3.1.1]decane): a water soluble compound that exhibits pH dependent DNA binding providing selectivity for diseased cells," Chem. Commun., pp. 1396-1397, 2001.
Top et al., "Synthesis, Biochemical Properties and Molecular Modelling Studies of Organometallic Specific Estrogen Receptor Modultors (SERMs), the Ferrocifens and Hydroxyferrocifens: Evidence for an Antiproliferative Effect of Hydroxyferrocifens on both Hormone-Dependent and Hormone-Independent Breast Cancer Cell Lines," Chem. Eur. J., vol. 9, pp. 5223-5236, 2003.

(Continued)

*Primary Examiner* — Anna Pagonakis
(74) *Attorney, Agent, or Firm* — Foley & Lardner LLP

(57) ABSTRACT

The present invention relates to compounds of the following formula (I):

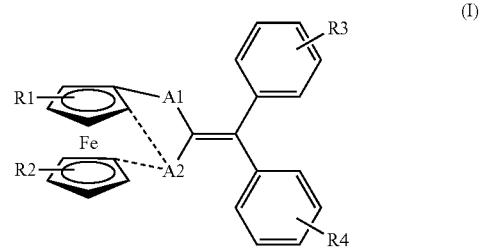

and to the pharmaceutically acceptable salts thereof, to the isomers and the mixtures of isomers thereof and to the water-soluble derivatives thereof, as well as to the method for preparing same and to the use thereof, particularly in the treatment of cancer.

17 Claims, No Drawings

OTHER PUBLICATIONS

Vessières et al., "Modification of the Estrogenic Properties of Diphenols by the Incorporation of Ferrocene. Generation of Antiproliferative Effects in Vitro," Journal of Medicinal Chemistry, vol. 48, No. 12, pp. 3937-3940.

Top et al., "Studies on organometallic selective estrogen receptor modulators. (SERMs) Dual Activity in the hydroxyl-ferrocifen series," Journal of Organometallic Chemistry, pp. 500-506, 2001.

Turbitt et al., "The Synthesis of [3]Ferrocenophan-1-One From Ferrocene by a Novel One-Step Annelation Reaction," Journal of Organometallic Chemistry, vol. 46, pp. 109-117, 1972.

Rosenblum et al., "The Structure and Chemistry of Ferrocene. VII. Bridged Ferrocenes," J. Am. Chem. Soc., vol. 85, pp. 316-324, 1963.

Mock et al., "The Synthesis of Bridged Ferrocene Derivatives with Functional Groups on the β-Carbon of the Bridge," J. Org. Chem., vol. 27, pp. 4050-4051, 1962.

Locke et al., "Asymmetric Synthesis of [3](1,1')- and [3](1,1')[3](3,3')-Ferrocenophanes," Organometallics, vol. 18, pp. 3750-3759, 1999.

Bickert et al., "Pentafulvenes: Versatile Synthons in Metallocene Chemistry," Organometallics, vol. 3, No. 5, pp. 653-657, May 1984.

Nguyen et al., "Nanoparticles loaded with ferrocenyl tamoxifen derivatives for breast cancer treatment, International Journal of Pharmaceutics," vol. 347, pp. 128-135, 2008.

Hillard et al., "Ferrocene-Mediated Proton-Coupled Electron Transfer in a Series of Ferrocifen-Type Breast-Cancer Drug Candidates," Angew. Chem. Int. Ed., vol. 45, pp. 285-290, 2006.

Schatzschneidr et al., "New Principles in Medicinal Organometallic Chemistry," Angew. Chem., Int. Ed., vol. 45, pp. 1504-1507, 2006.

Gormen et al.,"Synthesis, Cytotoxicity, and Compare Analysis of Ferrocene and [3] Ferrocenophane Tetrasubstituted Olefin Derivatives against Human Cancer Cells," ChemMedChem, vol. 5, Issue 12, pp. 2039-2050, 2010.

* cited by examiner

FERROCENE DERIVATIVES WITH ANTICANCER ACTIVITY

The present invention relates to ferrocene derivatives useful for the treatment of cancer, as well as the process for preparing them and their uses.

The advantage of using metal-coordinated derivatives in medicine has been restored by Rosenberg's discovery of anticancer effects of cisplatin (Rosenberg, B. et al. *Nature* 1969, 222, 385-386; Rosenberg, B. et al. *Nature* 1965, 205, 698-699; Wong, E. et al. *Chem. Rev.* 1999, 99, 2451-2466). Currently four classes of these types of coordination complex representatives are commercially available. These are as follows:

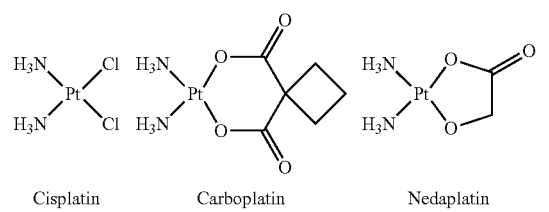

Cisplatin　　　Carboplatin　　　Nedaplatin

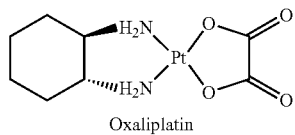

Oxaliplatin

Upon hydrolysis, they initially act by combining directly with DNA so as to prevent cell replication (Lippert, B. *Cisplatin: Chemistry and Biochemistry of a Leading Anticancer Drug*. John Wiley and Sons: New York, 1999.). However, despite their therapeutic value, these complexes suffer from several deficiencies such as severe systemic toxicity, and a relatively narrow therapeutic efficacy range.

It is however possible to introduce new paradigms in the field of metallodrugs by taking advantage of the versatility of organometal chemistry which provided the opening of a new interface (Vessières, A. et al. *Dalton Trans.* 2006, 4, 529-541; Jaouen, G. et al. Organometallics targeted to specific biological sites: The development of new therapies. In *Bioorganometallics*, Jaouen, G., Ed. Wiley-VCH: Weinheim, 2005; pp 65-95).

Thus, ferrocene compounds which are structural analogs of chloroquine, a drug that is unfortunately resistant to new strains of malaria, showed an antimalarial activity while being able to overcome this resistance, thus resulting in ferroquine, i.e. one of these ferrocene compounds, being in clinical phase IIb at Sanofi-Aventis. Likewise, two arene complexes of ruthenium (A) and (B) have just entered clinical trials as antimetastatics (Wand, F. et al. *Inorg. Chem.* 2002, 41, 4509-4523; Allardyce, C. S. et al. *Chem. Commun.* 2001, 1396-1397).

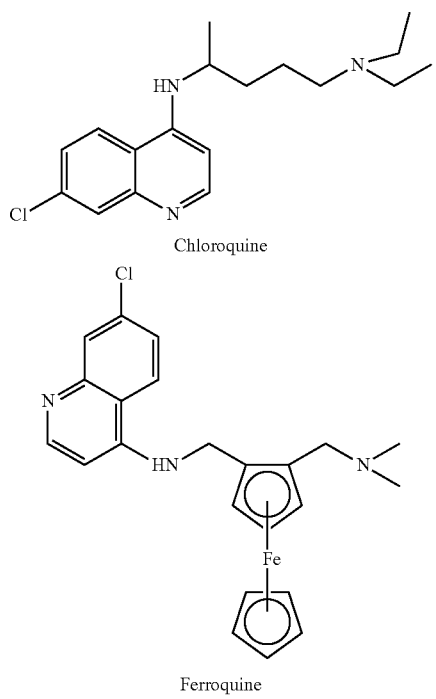

Chloroquine

Ferroquine

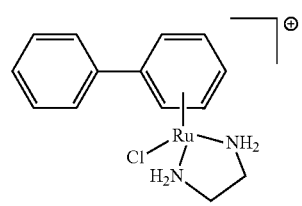

(A)

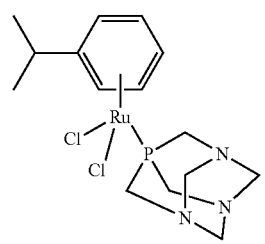

(B)

Likewise, molecules 1, 2 and 3 below have been tested in vitro (Top, S. et al. *Chem. Eur. J.* 2003, 9, 5223-5236; Vessières, A. et al. *J. Med. Chem.* 2005, 48, 3937-3940; Top, S. et al. *Organomet. Chem.* 2001, 637, 500-506).

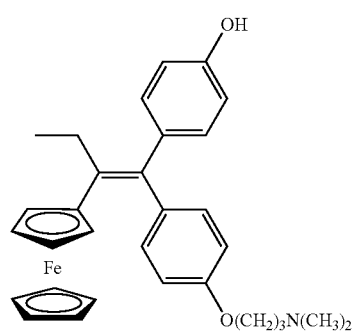

1

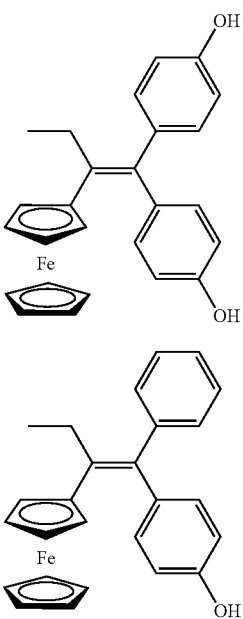

Thus, molecule 1 is partly similar in its effects to tamoxifen since it has the same type of antiestrogen activity on hormone-dependent breast tumors (ER+type) but is different from the latter in its antiproliferative behavior on non-hormone-dependent tumors (ER−).

Molecules 2 and 3, on the other hand, display antiproliferative activity on lines of breast cancers (MCF-7, MDA-MB-231) and prostate cancers (PC-3, DU-145).

Unfortunately the above-mentioned open molecules 1, 2 and 3, are still not optimum as such for a likely development.

The inventors have thus surprisingly discovered a new family of ferrocene derivatives having an anticancer activity higher than that of molecules 1, 2 or 3 by a factor of 10 to 20, especially on lines of cancer cells which do not include estrogen receptors α (corresponding to non-hormone-dependent cancers).

The present invention therefore provides a compound of the following formula (I):

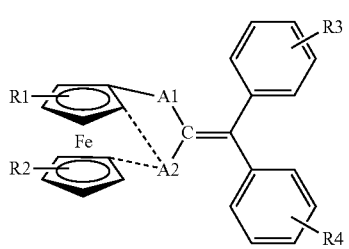

or a pharmaceutically acceptable salt thereof, an isomer or a mixture of isomers in any ratio, in particular a mixture of enantiomers, and more particularly a racemic mixture, or a water-soluble derivative,
wherein:
A1 and A2 are, independently from each other, either a bond between the cyclopentadienyl and the double bond carbon, or a linear alkyl chain comprising n1 and n2 carbon atoms, respectively, optionally substituted with one or more group(s) selected from halogen; phenyl optionally substituted with OH; ($C_1$-$C_6$) alkyl optionally substituted with one or more halogen(s); and ($C_3$-$C_6$) cycloalkyl optionally substituted with one or more halogen(s),
wherein n1 and n2 are, independently from each other, an integer comprised between 1 and 4,
with the proviso that A1 and A2 are not simultaneously a bond and that the A1-C-A2 chain contains at least 3 carbon atoms, and preferably 3, 4 or 5 carbon atoms,
——— is absent or represents a bond, with the proviso that A2 is linked to only one cyclopentadienyl group,
R1 and R2 each represent hydrogen or together form a linear alkyl chain connecting the two cyclopentadienyl groups and having 3 to 5 carbon atoms, wherein said chain is optionally substituted with one or more group(s) selected from halogen; phenyl optionally substituted with OH; ($C_1$-$C_6$)alkyl optionally substituted with one or more halogen(s); and ($C_3$-$C_6$)cycloalkyl optionally substituted with one or more halogen(s), and
R3 and R4 are, independently from each other, hydrogen or a $CF_3$, CN, $OR^5$ or $NR^6R^7$ group,
wherein:
$R^5$ represents hydrogen or a —CO—($C_1$-$C_{20}$)alkyl or —(CH2)$_m$$NR^8R^9$ group,
$R^6$, $R^7$, $R^8$ and $R^9$ are, independently from one another, hydrogen or a ($C_1$-$C_6$)alkyl or acyl group, and
m is an integer comprised between 2 and 8.

Thus, the molecules of the invention correspond to the following formula (Ia) or (Ib):

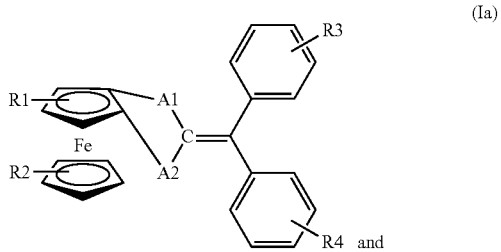

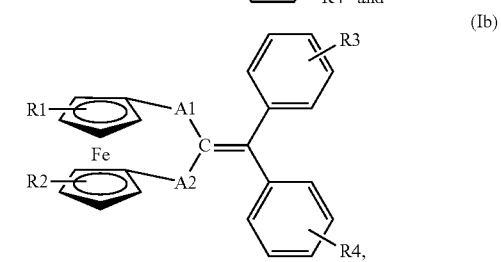

wherein R1, R2, R3, R4, A1 and A2 are as defined above.

Advantageously, the molecules of the invention will correspond to the formula (Ib).

The term <<A1-C-A2>> chain should be understood as designating the chain formed by the two moieties A1 and A2 and the carbon atom of the double bond linked to these two moieties.

In the present invention, <<pharmaceutically acceptable>> should be understood as designating what is useful in the preparation of a pharmaceutical composition, what is generally safe, non toxic and neither biologically nor otherwise undesired, and what is acceptable both for veterinary use and human pharmaceutics.

<<Pharmaceutically acceptable salts>> of a compound is understood as meaning salts which are pharmaceutically acceptable, as defined herein, and which have the desired pharmacological activity of the parent compound. Such salts include:

(1) hydrates and solvates, (2) acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like. Advantageously, it is the hydrochloric acid; or (3) salts formed when an acidic proton present in the parent compound either is replaced with a metal ion, for example an alkali metal ion, an alkaline earth metal ion; or is coordinated with an organic or inorganic base. Suitable organic bases include diethanolamine, ethanolamine, N-methylglucamine, triethanolamine, tromethamine and the like. Suitable inorganic bases include aluminum hydroxide, calcium hydroxide, potassium hydroxide, sodium carbonate and sodium hydroxide. Advantageously, the acidic proton is displaced with an $Na^+$ ion, especially with the use of sodium hydroxide.

In the present invention, the term <<isomers>>, within the meaning of the present invention, should be understood as designating diastereoisomers or enantiomers. Thus these are configuration isomers also known as <<stereoisomers>>. Stereoisomers which are not mirror images of each other are thus referred to as <<diastereoisomers>>, and stereoisomers which are mirror images of each other but that cannot be superimposed are referred to as <<enantiomers>>, also known as <<optical isomers>>.

A carbon atom linked to four non identical substituents is referred to as a <<chiral center>>. A molecule having such a chiral center is said to be chiral and has two enantiomer forms. A molecule having several chiral centers thus has several diastereoisomer and enantiomer forms.

An equimolar mixture of two enantiomers is called a racemic mixture.

The term <<water-soluble derivative>> should be understood as designating, within the meaning of the present invention, compounds of the formula (I) wherein R3 and R4 are such that they provide an increase in water-solubility of the compound and thus its bioavailability. Such compounds will be in particular compounds of the formula (I) in which R3 and/or R4 represent(s) an hydroxyl group esterified or coupled to a water-soluble species, such as a sugar or a water-soluble polymer.

The term <<sugar>> should be understood as including in particular, within the meaning of the present invention, erythrose, threose, ribose, arabinose, xylose, lyxose, allose, altrose, glucose, mannose, gulose, idose, galactose, talose, erythrulose, ribulose, xylulose, psicose, fructose, sorbose or also tagatose, either in D or L form. Advantageously, it is glucose or rhamnose.

The term <<water-soluble polymer>> should be understood as including in particular, within the meaning of the present invention, a dendrimer or a polyethylene glycol (PEG) derivative. A dendrimer can be in particular a polyamidoamide (PAMAM) type dendrimer.

In particular, R3 and/or R4 can represent a chain derived from PEG of the formula $—COCH_2X^1CH_2COX^2(CH_2CH_2O)_pCH_2CH_2X^3$, where:

$X^1$ represents a direct bond, an oxygen atom or a $CH_2$ or $CH_2—CH_2$ group, $X^2$ represents an oxygen atom or NH, $X^3$ represents $OR^{11}$ or $NR^{12}R^{13}$, $R^{11}$ is hydrogen or $(C_1-C_6)$alkyl, $R^{12}$ and $R^{13}$ are, independently from each other, hydrogen or $(C_1-C_6)$alkyl, m is an integer comprised between 2 and 8, and p is an integer comprised between 1 and 20.

The term <<alkyl chain>> should be understood as designating, within the meaning of the present invention, any saturated, linear or branched hydrocarbon group, except otherwise stated.

The term <<$(C_1-C_6)$alkyl>> should be understood as designating, within the meaning of the present invention, an alkyl group as defined above having from 1 to 6 carbon atoms, and advantageously from 1 to 4 carbon atoms, in particular methyl, ethyl, n-propyl, isopropyl, n-butyl, iso-butyl, sec-butyl and tert-butyl groups.

The term <<$(C_1-C_{20})$alkyl>> should be understood as designating, within the meaning of the present invention, an alkyl group as defined above having from 1 to 20 carbon atoms.

The term <<$(C_3-C_6)$cycloalkyl>> should be understood as designating, within the meaning of the present invention, a saturated hydrocarbon cycle having from 3 to 6 carbon atoms and more preferably 3 or 4 carbon atoms, in particular a cyclopropyl or cyclobutyl group.

The term <<acyl>> should be understood as designating, within the meaning of the present invention, a group of the formula $—CO—R$ where R represents $(C_1-C_6)$alkyl as defined above.

The term <<halogen>> should be understood, within the meaning of the present invention, as being a fluorine, bromine, chlorine or iodine atom. Advantageously, it refers to a fluorine, bromine or chlorine atom.

Advantageously, at least one of R3 and R4 is not a hydrogen, and even more advantageously, both R3 and R4 are not a hydrogen.

In one embodiment, R3 and/or R4, independently from each other, are $OR^5$, where $R^5$ is as defined above, and is preferably hydrogen.

Advantageously, R3 and R4, independently from each other, are $OR^5$, where $R^5$ is as defined above, and is preferably hydrogen.

Even more advantageously, R3 and R4 represent OH.

In one further embodiment, R3 and/or R4 are located in the para-position on the phenyl ring.

Advantageously, R3 and R4 are located in the para-position on the phenyl ring.

Even more advantageously, R3 and R4 are located in the para-position on the phenyl ring and represent OH.

In one further embodiment, R1 and R2 each represent a hydrogen atom.

Advantageously, A1 and A2 represent linear alkyl chains having n1 and n2 carbon atoms, respectively, optionally substituted with $(C_1-C_6)$alkyl.

According to a preferred embodiment, the A1-C-A2 chain contains at most 5 carbon atoms. Thus, the A1-C-A2 chain will advantageously contain 3, 4 or 5 carbon atoms, and advantageously 3 carbon atoms.

Even more advantageously, A1 or A2 represents a bond.

The compound according to the invention can be selected in particular from molecules of the following formulae 4 to 11:

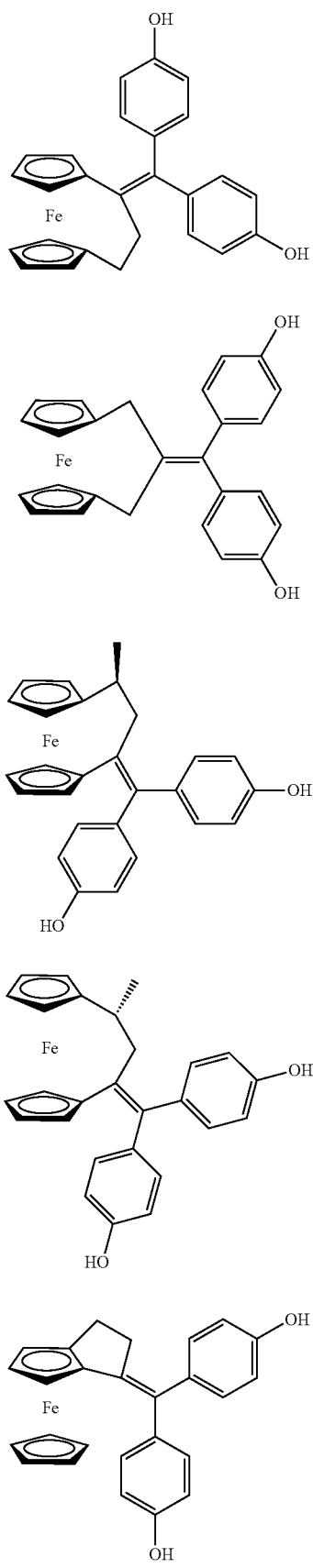
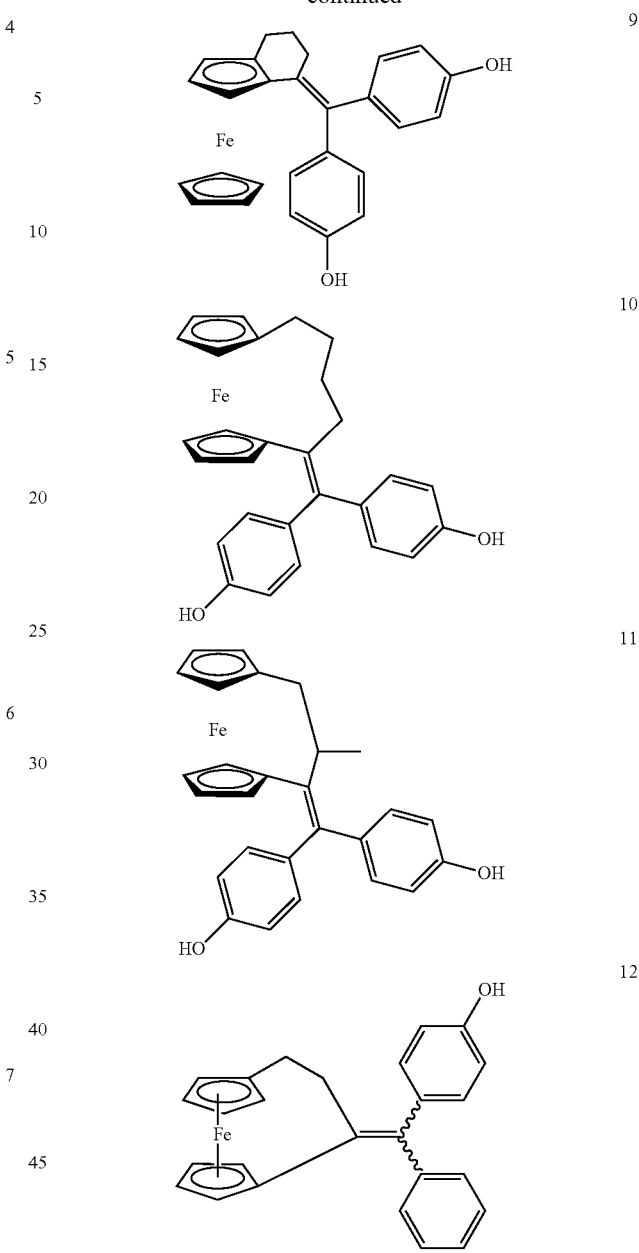

The present invention also provides compounds of the formula (I) as defined above for their use as a medicine.

They can be useful in particular as an antiproliferative medicine, especially in the treatment or prevention of cancer, and in particular breast and prostate cancer. Even more advantageously, the compounds of the invention are useful in the treatment or prevention of breast cancer, and preferably non-hormone-dependent breast cancer.

The present invention further relates to the use of a compound of the formula (I) as defined above for the manufacture of a medicine, especially for the treatment or prevention of proliferative diseases such as cancer, and in particular, such as breast or prostate cancer. Even more advantageously, the compounds of the invention are used in the treatment or prevention of breast cancer, and preferably non-hormone-dependent breast cancer.

The present invention further relates to a method for the treatment or prevention of a proliferative disease, such as cancer, and in particular breast or prostate cancer, and advantageously breast cancer, preferably non-hormone-dependent breast cancer, comprising administering a sufficient amount of a compound of the formula (I) according to the invention to a patient in need thereof.

The present invention also provides a pharmaceutical composition comprising at least one compound of the formula (I) as defined above, in combination with a pharmaceutically acceptable vehicle.

This pharmaceutical composition can include at least one additional active ingredient, which can be in particular an anticancer compound advantageously selected from 6-mercaptopurin, fludarabin, cladribin, pentostatin, cytarabin, 5-fluorouracil, gemcitabin, methotrexate, raltitrexed, irinotecan, topotecan, etoposide, daunorubicin, doxorubicin, epirubicin, idarubicin, pirarubicin, mitoxantrone, chlormethin, cyclophosphamide, ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, bicalutamide, cyprotcrone acctate, triptorelin, leuprorelin, goserelin, buserelin, formestane, aminoglutethimide, anastrazole, letrozole, tamoxifen, octreotide and lanreotide.

The compounds according to the invention can be administered orally, sublingually, parenterally, subcutaneously, intramuscularly, intravenously, transdermally, topically or rectally.

In the pharmaceutical compositions of the present invention to be administered orally, sublingually, parenterally, subcutaneously, intramuscularly, intravenously, transdermally, topically or rectally, the active ingredient can be administered in unit dosage forms, as a mixture with conventional pharmaceutical carriers, to animals or humans. Suitable unit dosage forms include oral forms such as tablets, capsules, powders, granules, and oral solutions or suspensions, sublingual and buccal dosage forms, parenteral, subcutaneous, intramuscular, intravenous, intranasal or intraocular dosage forms, and rectal dosage forms.

For preparing a solid composition in the form of a tablet, the main active ingredient is mixed with a pharmaceutical vehicle such as gelatin, starch, lactose, magnesium stearate, talc, gum arabic or the like. The tablets can be coated with sucrose or other suitable materials or can also be processed in order to have an sustained or delayed activity and so as to continuously deliver a predetermined amount of active ingredient.

A preparation in the form of capsules is obtained by mixing the active ingredient with a diluent and by filling the resulting mixture into soft or hard gelatin capsules.

A preparation in the form of syrups or elixirs can contain the active ingredient together with a sweetener, an antiseptic agent, as well as a flavoring agent and a suitable colorant.

Water-dispersible powders or granules can contain the active ingredient in a mixture with dispersing agents or wetting agents, or suspending agents, as well as with taste modifiers or sweeteners.

For rectal administration, suppositories are employed which are prepared with binders melting at rectum temperature, for example cocoa butter or polyethylene glycols.

For parenteral, intranasal or intraocular administration, aqueous suspensions, isotonic saline solutions or sterile solutions for injection containing pharmacologically compatible dispersing agents and/or wetting agents are used.

The active ingredient can further be formulated in the form of microcapsules or nanocapsules, optionally with one or more additive carriers.

The compounds of the invention can be used at daily doses in the range of between 0.01 mg and 1000 mg, taken in one single dosage once a day or divided into several individual doses given at intervals during the day, for example twice a day in equal doses. The daily dosage is advantageously in the range of between 5 mg and 500 mg, even more advantageously between 10 mg and 200 mg. It may be necessary to use dosages outside these ranges in a manner known to the person skilled in the art.

The present invention also provides a pharmaceutical composition comprising:
   (i) at least one compound of the formula (I) as defined above, and
   (ii) at least one additional active ingredient,
as combination products to be administered simultaneously, separately or sequentially.

In fact, dual- or tri-therapies are conventionally used for treating cancer. The active ingredient used is advantageously an anticancer compound.

Examples of active principles that can be combined with a compound of the formula (I) in a composition according to the invention include but are not limited to 6-mercaptopurin, fludarabin, cladribin, pentostatin, cytarabin, 5-fluorouracil, gemcitabin, methotrexate, raltitrexed, irinotecan, topotecan, etoposide, daunorubicin, doxorubicin, epirubicin, idarubicin, pirarubicin, mitoxantrone, chlormethin, cyclophosphamide, ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, hicalutamide, cyproterone acetate, triptorelin, leuprorelin, goserelin, buscrelin, formestan, aminoglutethimide, anastrazole, letrozole, tamoxifen, octreotide and lanreotide.

The present invention also provides a pharmaceutical composition comprising:
   (i) at least one compound of the formula (I) as defined above, and
   (ii) at least one additional active ingredient,
as combination products to be administered simultaneously, separately or sequentially,
for use as an antiproliferative drug, especially for the treatment or prevention of cancer, and in particular breast and prostate cancer. Even more advantageously, the medicine is designed for the treatment or prevention of breast cancer, preferably non-hormone-dependent breast cancer.

The present invention also provides the use of a compound of the formula (I) as defined above, for the manufacture of a medicine to be administered alone or in combination, simultaneously, separately or sequentially, with ionizing or non-ionizing radiations, for the treatment or prevention of a proliferative disease such as cancer, and in particular breast or prostate cancer, and more advantageously breast cancer, especially non-hormone-dependent breast cancer.

The present invention further relates to a method for the treatment of a proliferative disease, such as cancer, and in particular breast or prostate cancer, and even more advantageously breast cancer, especially non-hormone-dependent breast cancer, comprising administering a sufficient amount of a compound of the formula (I) as defined above, alone or in combination, simultaneously, separately or sequentially, with ionizing or non-ionizing radiations, to a patient in need thereof.

The radiations used can be in particular X rays or gamma rays, which radiations are commonly used in radiotherapy for the treatment of cancer.

The present invention also provides a process for the preparation of a compound of the formula (I) as defined above comprising the following steps:
(i) McMurry coupling of a compound of the following formula (II):

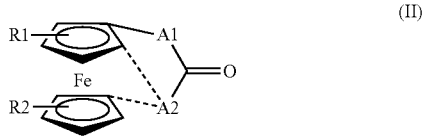

wherein R1, R2, A1 and A2 are as defined above, with a compound of the following formula (III):

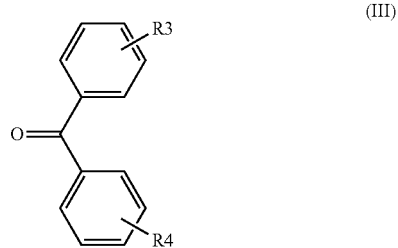

wherein R3 and R4 are as defined above,
to form the compound of the formula (I),
(ii) recovering the compound of the formula (I), obtained in step (i) above.

Said McMurry coupling can be optionally followed with a reaction of deprotection and/or modification and functionalization of R3 and R4 by conventional methods well known to those skilled in the art.

The compound of the invention may be recovered by methods well known to those skilled in the art, especially by filtration or evaporation of the solvent, especially under vacuum. Washing steps of the organic layer containing the compound of the invention and extraction steps can be carried out beforehand.

The product obtained can be purified if necessary by conventional purification methods well known to those skilled in the art, such as a recrystallization, preparative thin layer chromatography, high performance liquid chromatography (commonly known as HPLC) or silica gel column chromatography. Advantageously, the preferred method is recrystallization when the product is crystalline and/or silica gel column chromatography.

McMurry coupling is described in particular in the following publications: Nakayama J. et al. *Chem. Com.* 1986, 12, 974-975; Top S. et al. *Chem. Eur. J.* 2003, 9, 5223-5236; Vessieres A. et al. *J. Med. Chem.* 2005, 48, 3937-3940; or Hillard E. A. et al. *Dalton Transactions* 2007, 43, 5073-5081.

McMurry coupling employs as a reagent a titanium complex having a low valency number, such as $TiCl_4$ or $TiCl_3$, in the presence of a reducing agent, such as lithium, sodium, magnesium, zinc, $LiAlH_4$, or Zn—Cu amalgam.

Preferably, the McMurry coupling reaction is conducted in the presence of $TiCl_4$ and zinc, preferably in the form of a powder, and particularly in the presence of pyridine.

The compound of the formula (II) can be obtained by methods well known to those skilled in the art and more particularly described in the following articles: Turbitt T. D. et al. *J. of Organomet. Chem.* 1972, 46, 109-117; Rosenblum M. et al. *J. Am. Chem. Soc.* 1963, 85, 316-324; Movk W. et al. *J. Org. Chem.* 1962, 27, 4050-4051; Locke A. J. et al. *Organometallics* 1999, 18, 3750-3759; Bickert P. et al. *Organometallics* 1984, 3, 653-657; Kenneth L. et al. *J. Am. Chem. Soc.* 1962, 84(17), 3263-3269 and Radovan Sebesta et al. *Tetrahedron Asymmetry* 2007, 18(16), 1893-1898.

The compound of the formula (III) can be either commercially available, or prepared by methods well known to those skilled in the art. In particular, 4,4'-dihydroxybenzophenone is sold by Alfa Aeser.

The following examples are intended to better illustrate the present invention but are not to be construed as limiting its scope.

EXAMPLES

Abbreviations used:
NMR Nuclear Magnetic Resonance
IR Infra Red
MS Mass Spectrometry
HR-MS High Resolution Mass Spectrometry Example 1

Preparation of Compounds of the Invention 1.1. Preparation of 1,1'-[1-[1,1-bis(4-hydroxyphenyl)methylidene]trimethylene]ferrocene (4)

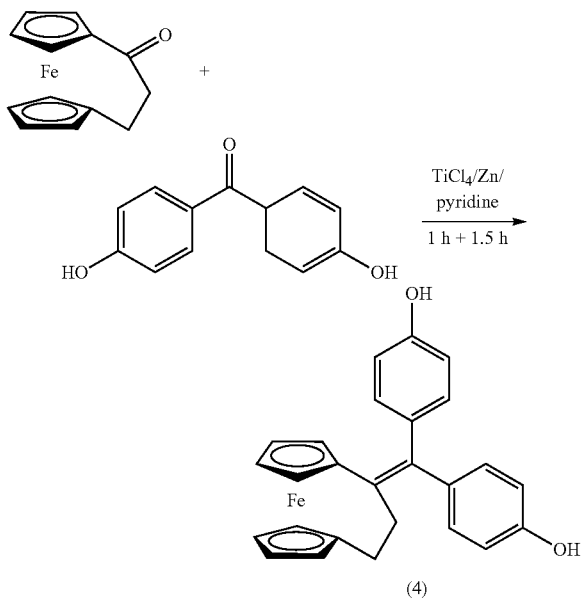

To a suspension of 3.07 g (0.0469 mmol) of zinc powder in 100 cm³ of anhydrous tetrahydrofuran (THF), are added 4.51 g (2.61 cm³; 0.024 mol) of $TiCl_4$ under stirring at −10° C. The cooling bath is then removed and the reaction mixture is refluxed for 60 min. After cooling to room temperature (RT), 3.79 g (3.86 cm³; 0.0479 mol) of anhydrous pyridine are added and the mixture is stirred for 5 min at RT. A solution of 1.92 g (0.008 mol) of [3]ferrocenophan-1-one (prepared according to Turbitt T. D. et al. *J. of Organomet. Chem.* 1972, 46, 109-117 or Rosenblum M. et al. *J. Am. Chem. Soc.* 1963, 85, 316-324) and 1.71 g (0.008 mol) of 4,4'-dihydroxybenzophenone in 30 cm³ of anhydrous THF is then added and the reaction mixture is refluxed for 90 min. After cooling to room temperature, the resulting mixture is hydrolyzed with 100 cm³ of an 8% aqueous solution of potassium carbonate. The reaction mixture is extracted several times with 100 cm³ of diethyl ether. The organic layer is washed with water (2×200 ml) and brine (200 ml), dried over magnesium sulfate and evaporated to dryness. Product 1 is isolated by flash chromatography on silica gel (800 ml, eluting with n-pentane-diethyl ether 2:1) with a 46.50% yield (90-95% pure).

If necessary, Compound 4 thus obtained can be purified by means of a second flash chromatography using 60 ml of silica gel and a 4:1 mixture of n-pentane-diethyl ether as an eluent, to yield a yellow powder which is recrystallized from a mixture of ethyl acetate (5 ml)-n-pentane (80 ml) at 4° C. After 48 hr, the organic solution is discarded and the yellow crystals obtained are washed with pentane twice to give Compound 4 in pure form, with a yield of 28.14%.

Alternatively, the raw material can be dissolved in a minimum amount of hot acetone and left to crystallize for 24 hr at −20° C. The solvent is decanted off and the crystals obtained are washed with 10 ml of n-pentane twice to yield 1.10 g of Compound 4 in pure form.

$^1$H NMR (300.13 MHz, acetone-$d_6$): 8.31 (s, 1H, OH); 8.10 (s, 1H, OH); 7.07 (d, J=8.40 Hz, 2H, Ar); 6.85 (d, J=8.70 Hz, 2H, Ar); 6.84 (d, J=8.70 Hz, 2H, Ar); 6.54 (d, J=8.70 Hz, 2H, Ar); 4.25 (t, J=1.80 Hz, 2H, Cp); 3.98 (m, 4H, Cp); 3.92 (t, J=1.50 Hz, 2H, Cp); 2.70 (m, 2H, CH$_2$); 2,34 (m, 2H, CH$_2$)
$^{13}$C NMR (75.48 MHz, acetone-$d_6$): 156.95; 156,35; 141.41; 136,36; 132.40; 131.14; 115.68; 114.82; 87.62; 84.89; 70.96; 70.83; 69.14; 68.78; 41.50; 29.14
Analysis: Calculated for $C_{26}H_{22}FeO_2$: C—73.95%, H—5.25%, Found: C—73.79%, H—5.34%
MS (IC—CH$_4$): 423.1 (M+H)$^+$; 422.1 (M)$^+$;
HR-MS (IC—CH$_4$): found: 423.1040 (M+H)$^{+'}$ calculated for $C_{26}H_{23}FeO_2$ 423.1047 (M+H)$^+$ 1.2. Preparation of 1,1'-[2-[1,1-bis(4-hydroxyphenyl)methylidene]trimethylene]ferrocene (5)

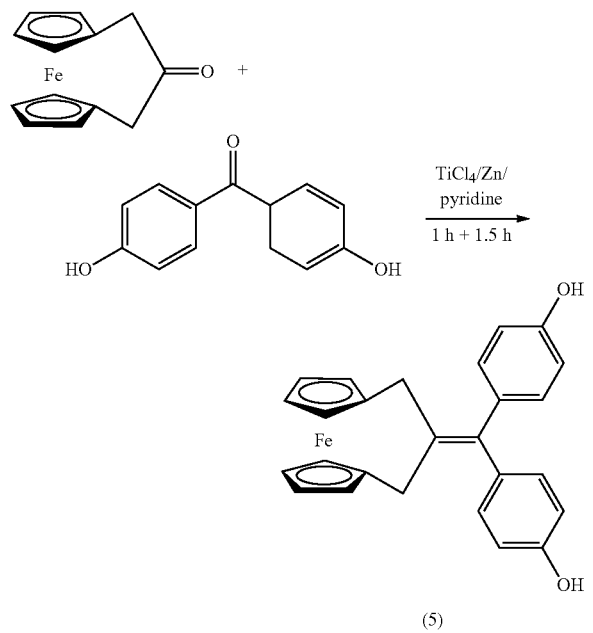

Compound 5 was prepared according to the procedure described for Compound 4 starting from 0.100 g (4.167×10$^{-4}$ mol) of 1,1'-(2-ketotrimethylene)-ferrocene (prepared according to Movk W. et al. *J. Org. Chem.* 1962, 27, 4050-4051), 0.0892 g (4.167×10$^{-4}$ mol) of 4,4'-dihydroxybenzophenone, 0.235 g (0.136 cm³, 1.250×10$^{-3}$ mol) of TiCl$_4$, 0.160 g (2.443×10$^{-3}$ mol) of zinc powder, 0.197 g (0.201 cm³, 2.500×10$^{-3}$ mol) of anhydrous pyridine and 5+1.5 cm³ of anhydrous tetrahydrofuran.

Compound 5 was isolated as a yellow powder by flash chromatography on silica gel (80 ml, eluting with n-pentane-diethyl ether 3:4) with a yield of 22%.

The compound thus obtained by chromatography can be further purified by dissolution in a minimum amount of hot acetone and leaving it to crystallize for 24 hr at −20° C. The solvent is decanted off and the crystals obtained are washed with 2 ml of n-pentane twice to yield 0.045 g of Compound 5 in pure form.

$^1$H NMR (300.13 MHz, acetone-$d_6$): 8.22 (s, 1H, OH); 7.16 (d, J=8.7 Hz, 2H, Ar); 6.80 (d, J=8.7 Hz, 2H, Ar); 4.11 (t, J=1.9 Hz, 2H, Cp); 3.99 (t, J=1.9 Hz, 2H, Cp); 2.81 (s, CH$_2$);
$^{13}$C NMR (75.48 MHz, acetone-d6): 156.66; 156.56; 141.67; 138.59; 135.80; 130.98; 115.73; 115.64; 83.52; 70.28; 69.23;
IR (KBr): 3407; 1609; 1508; 1430; 1220; 1197; 831
MS (IC—CH4): 423.1 (M+H)$^+$; 422.1 (M)$^+$;
HR-MS (IC—CH4): found: 423.1034 (M+H)$^{+'}$ calculated for $C_{26}H_{23}FeO_2$ 423.1047 (M+H)$^+$ 1.3. Preparation of (S)-1,1'-[1-[1,1-bis(4-hydroxyphenyl)methylidene]-3-methyltrimethylene]ferrocene (6)

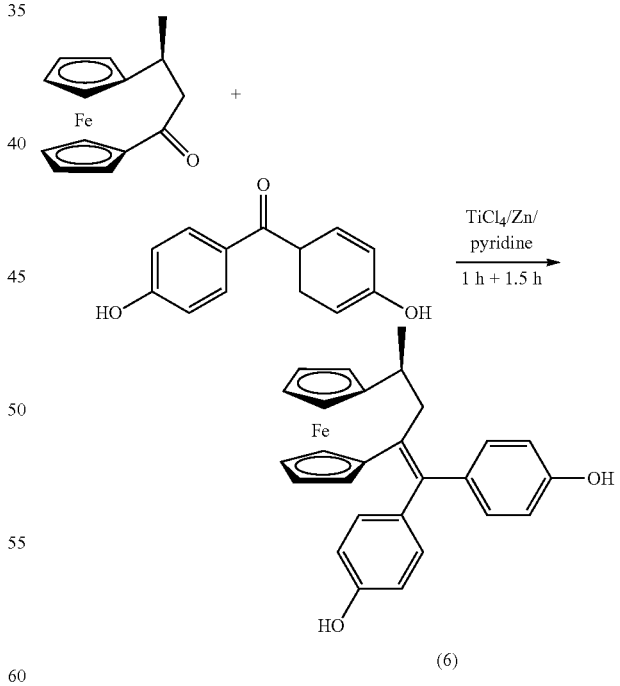

Compound 6 was prepared according to the procedure described for Compound 4 starting from 0.254 g (1×10$^{-3}$ mol) of (S)-1,1'(3-methyl-1-ketotrimethylene)ferrocene (prepared according to Locke A. J. et al. *Organometallics* 1999, 18, 3750-3759), 0.214 g (1×10$^{-3}$ mol) of 4,4'-dihydroxybenzophenone, 0.564 g (0.326 cm³, 3.000×10$^{-3}$ mol) of TiCl$_4$, 0.384 g (5.862×10$^{-3}$ mol) of zinc powder, 0.472 g (0.482 cm$^3$, 6.000×10$^{-3}$ mol) of anhydrous pyridine and 12+4 cm$^3$ of anhydrous tetrahydrofuran.

Compound 6 was isolated as a yellow powder by flash chromatography on silica gel (80 ml, eluting with n-pentane-diethyl ether 1:1) and recrystallization from a mixture of diethyl ether-pentane with a yield of 24.08%.

$^1$H NMR (300.13 MHz, acetone-d$_6$): 8.30 (s, 1H, OH); 8.09 (s, 1H, OH); 7.06 (d, J=8.7 Hz, 2H, Ar); 6.83 (d, J=8.7 Hz, 4H, Ar); 6.53 (d, J=8.7 Hz, 2H, Ar); 4.32 (m, 2H); 4.22 (m, 1H); 4.07 (m, 1H); 4.01 (m, 1H); 3.82 (m, 2H); 3.68 (m, 1H); 2.60 (m, 1H); 1.13 (d, J=6.4 Hz, 3H)

$^{13}$C NMR (75.48 MHz, acetone-d$_6$): 156.96; 156.38; 136.04; 135.86; 133.74; 132.43; 131.24; 130.43; 115.61; 114.85; 92.68; 86.90; 71.83; 69.98; 69.80; 69.22; 68.72; 67.51; 66.83; 66.07; 50.23; 36.23; 22.46; 15.57

1.4. Preparation of (R)-1,1'-[1-[1,1-bis(4-hydroxyphenyl)methylidene]-3-methyltrimethylene]ferrocene (7)

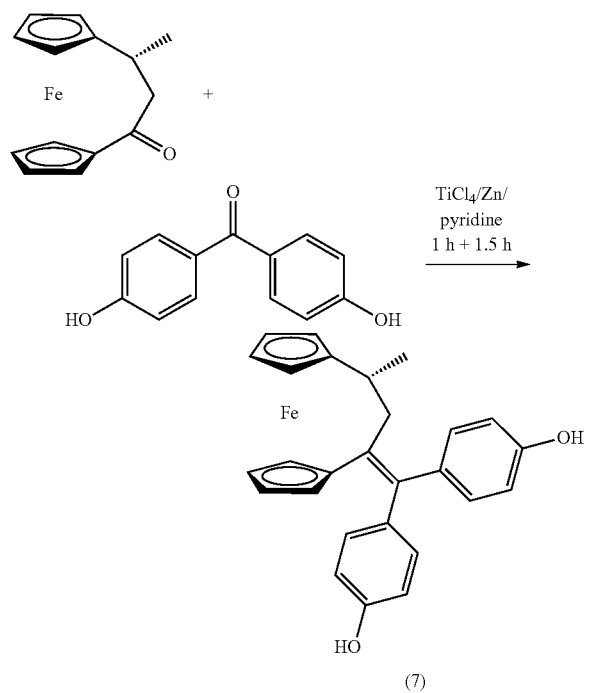

(7)

Compound 7 was prepared according to the procedure described for Compound 4 starting from 0.254 g (1×10$^{-3}$ mol) of (R)-1,1'(3-methyl-1-ketotrimethylene)ferrocene (prepared according to Locke A. J. et al. *Organometallics* 1999, 18, 3750-3759), 0.214 g (1×10$^{-3}$ mol) of 4,4'-dihydroxybenzophenone, 0.564 g (0.326 cm$^3$, 3.000×10$^{-3}$ mol) of TiCl$_4$, 0.384 g (5.862×10$^{-3}$ mol) of zinc powder, 0.472 g (0.482 cm$^3$, 6.000×10$^{-3}$ mol) of anhydrous pyridine and 12+4 cm$^3$ of anhydrous THF.

Compound 7 was isolated as a yellow powder by flash chromatography on silica gel (80 ml, eluting with n-pentane-diethyl ether 1:1) and recrystallization from a mixture of diethyl ether-pentane with a yield of 24.08%.

$^1$H NMR (300.13 MHz, acetone-d$_6$): 8.30 (s, 1H, OH); 8.09 (s, 1H, OH); 7.06 (d, J=8.7 Hz, 2H, Ar); 6.83 (d, J=8.7 Hz, 4H, Ar); 6.53 (d, J=8.7 Hz, 2H, Ar); 4.32 (m, 2H); 4.22 (m, 1H); 4.07 (m, 1H); 4.01 (m, 1H); 3.82 (m, 2H); 3.68 (m, 1H); 2.60 (m, 1H); 1.13 (d, J=6.4 Hz, 3H)

$^{13}$C NMR (75.48 MHz, acetone-d$_6$): 156.96; 156.38; 136.04; 135.86; 133.74; 132.43; 131.24; 130.43; 115.61; 114.85; 92.68; 86.90; 71.83; 69.98; 69.80; 69.22; 68.72; 67.51; 66.83; 66.07; 50.23; 36.23; 22.46; 15.57

1.5. Preparation of 1,2-[1-[1,1-bis(4-hydroxyphenyl)methylidene]trimethylene]ferrocene (8)

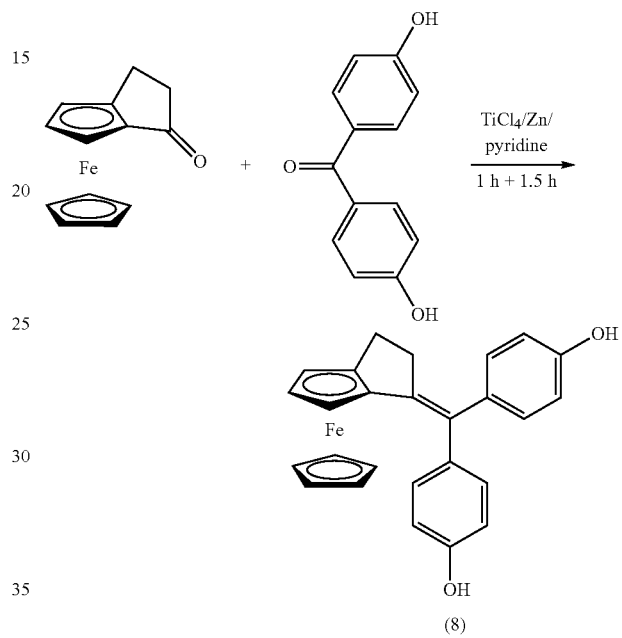

(8)

Compound 8 was prepared according to the procedure described for Compound 4 starting from 0.120 g (5×10$^{-4}$ mol) of 1,2-(1-ketotrimethylene)ferrocene (prepared according to Bickert P. et al. *Organometallics* 1984, 3, 653-657), 0.107 g (5×10$^{-4}$ mol) of 4,4'-dihydroxybenzophenone, 0.282 g (0.163 cm$^3$, 1.500×10$^{-3}$ mol) of TiCl$_4$, 0.192 g (2.931×10$^{-3}$ mol) of zinc powder, 0.236 g (0.241 cm$^3$, 3.000×10$^{-3}$ mol) of anhydrous pyridine and 6+1.8 cm$^3$ of anhydrous THF.

Compound 8 was isolated as an orange powder with a 30% yield by flash chromatography on silica gel (50 ml, eluting with n-pentane-diethyl ether 3:4) followed with a second chromatography using 80 ml of silica gel and a mixture of n-pentane-diethyl ether 1:1 as an eluent.

$^1$H NMR (300.13 MHz, acetone-d$_6$): 8.27 (s, 1H, OH); 8.24 (s, 1H, OH); 7.15 (d, J=8.7 Hz, 2H, Ar); 7.07 (d, J=8.7 Hz, 2H, Ar); 6.86 (d, J=8.7 Hz, 2H, Ar); 6.78 (d, J=8.7 Hz, 2H, Ar); 4.14 (m, 1H, Cp); 4.03 (s, 5H, Cp); 3.95 (m, 1H, Cp); 3.58 (m, 1H, CH$_2$); 3.16 (m, 1H, Cp); 2.90 (m, 1H, CH$_2$); 2.70 (m, 1H, CH$_2$); 2.49 (m, 1H, CH$_2$)

$^{13}$C NMR (75.48 MHz, acetone-d$_6$): 156.92; 156.50; 137.74; 135.60; 131.91; 131.61; 130.82; 130.43; 115.75; 115.49; 98.12; 91.64; 71.44; 70.59; 69.39; 62.92; 62.68; 37.08; 25.53

Analyses: Calculated for C$_{26}$H$_{22}$FeO$_2$: C—73.95%, H—5.25%, Found: C—73,61%, H—5.77%

MS (EI): 422 (M)$^+$

HR-MS (EI): found: 422.0953 (M)$^{+\cdot}$ calculated for C$_{26}$H$_{22}$FeO$_2$ 422.0969 (M)$^+$

1.6. Preparation of 1,2-[1-[1,1-bis(4-hydroxyphenyl) methylidene]tetramethylene]-ferrocene (9)

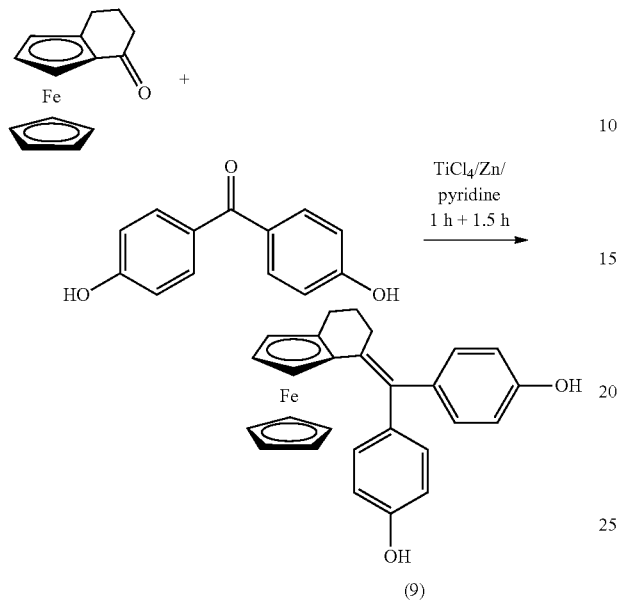

(9)

Compound 9 was prepared according to the procedure described for Compound 4 starting from 0.508 g ($2\times10^{-3}$ mol) of 1,2-(1-ketotetramethylene)ferrocene (prepared according to Kenneth L. et al. *J. Am. Chem. Soc.* 1962, 84(17), 3263-3269), 0.428 g ($2\times10^{-3}$ mol) of 4,4'-dihydroxybenzophenone, 1.128 g (0.658 cm$^3$, $6.00\times10^{-3}$ mol) of TiCl$_4$, 0.784 g ($11.724\times10^{-3}$ mol) of zinc powder, 0.944 g (0.970 cm$^3$, $12.00\times10^{-3}$ mol) anhydrous pyridine and 28+10 cm$^3$ of anhydrous THF.

Compound 9 was isolated by flash chromatography on silica gel (50 ml, eluting with n-pentane-diethyl ether 2:1).

Alternatively, Compound 9 can be purified by dissolving the raw material in a minimum amount of hot acetone and leaving it to crystallize for 24 hr at −20° C. The solvent is then decanted off and the crystals thus obtained are washed with 2 ml of n-pentane twice to yield 0.140 g (16%) of Compound 9 in pure form.

$^1$H NMR (700.45 MHz, acetone-d$_6$): 8.31 (s, OH); 8.35 (s, OH); 7.05 (d, J=8.4 Hz, 4H, Ar); 6.87 (m, 2H, Ar); 6.78 (d, J=8.8 Hz, 2H, Ar); 4.15 (s, 1H, Cp); 4.02 (s, 5H, Cp); 3.85 (t, J=2.2 Hz, 1H, Cp); 3.15 (m, 1H, Cp); 2.80-2.75 (m, 2H, CH$_2$); 2.41-2.34 (m, 2H, CH$_2$); 2.03-1.99 (m, 1H, CH$_2$); 1.67-1.63 (m, 1H, CH$_2$)

1.7. Preparation of 1,1'-[1-[1,1-bis(4-hydroxyphenyl) methylidene]pentamethylene]ferrocene (10)

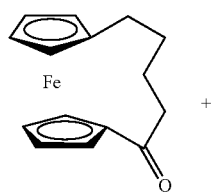

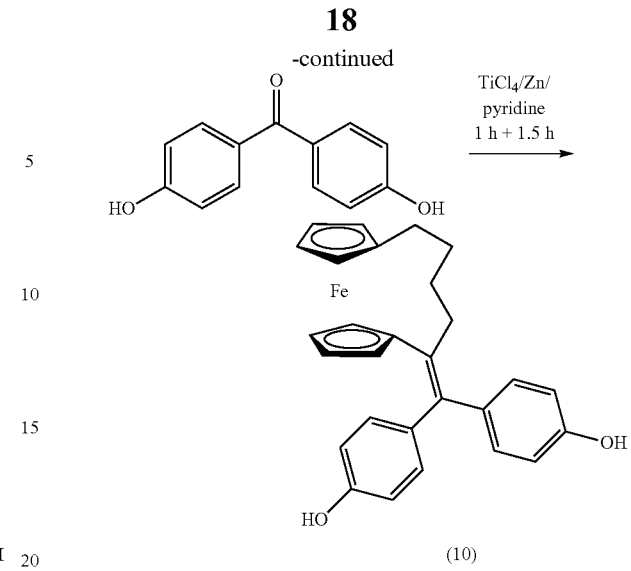

(10)

Compound 10 was prepared according to the procedure described for Compound 4 starting from 1,1'-(1-ketopentamethylene)ferrocene (prepared according to Radovan Sebesta el al. *Tetrahedron Asymmetry* 2007, 18(16), 1893-1898), 0.214 g ($1\times10^{-3}$ mol) of 4,4'-dihydroxybenzophenone, 0.564 g (0.329 cm$^3$, $3.00\times10^{-3}$ mol) of TiCl$_4$, 0.392 g ($5.862\times10^{-3}$ mol) of zinc powder, 0.472 g (0.485 cm$^3$, $12.00\times10^{-3}$ mol) of anhydrous pyridine and 14+5 cm$^3$ of anhydrous THF.

Compound 10 was isolated by flash chromatography on silica gel (70 ml, eluting with n-pentane-diethyl ether 2:1).

Alternatively, Compound 10 can be purified by dissolving the raw material in a minimum amount of hot acetone and leaving it to crystallize for 24 hr at −50° C. The solvent is then decanted off and the crystals thus obtained are washed with 2 ml of n-pentane twice to yield 0.050 g (11%) of Compound 10 in pure form.

$^1$H NMR (700.45 MHz, acetone-d$_6$): 8.21 (s, 1H, OH); 8.12 (s, 1H, OH); 7.06 (d, J=8.8 Hz, 2H, Ar); 6.82 (d, J=8.8 Hz, 2H, Ar); 6.81(d, J=8.8 Hz, 2H, Ar); 6.66 (d, J=8.8 Hz, 2H, Ar); 4.06 (t, J=1.8 Hz, 2H, Cp); 4.04 (t, J=1.8 Hz, 2H, Cp); 3.96 (t, J=1.8 Hz, 2H, Cp); 3.82 (t, J=1.8 Hz, 2H, Cp); 2.60 (t, J=6.6 Hz, 2H, CH$_2$); 2.51 (t, J=6.6 Hz, 2H, CH$_2$); 2.27 (m, 2H, CH$_2$); 1.91 (m, 2H, CH$_2$)

$^{13}$C NMR (176.15 MHz, acetone-d$_6$): 139.22; 136.62; 136.45; 133.62; 130.56; 114.82; 88.02; 85.93; 69.97; 68.88; 67.32; 67.03; 31.58; 25.60; 25.17; 23.74

1.8. Preparation of 1,1'-[1-[1,1-bis(4-hydroxyphenyl) methylidene]-2-methyltrimethylene]ferrocene (11)

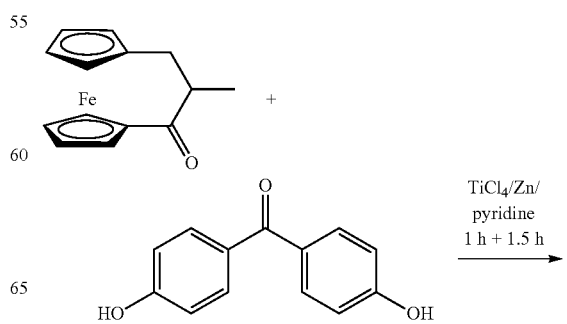

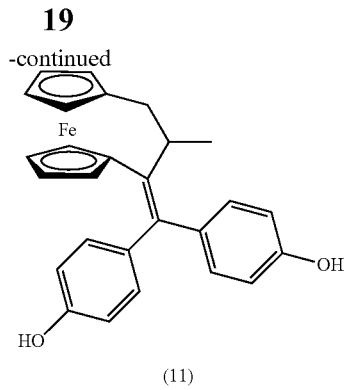

(11)

Compound 11 was prepared according to the procedure described for Compound 4 starting from 0.254 g (1×10⁻³ mol) of 1,1'-(2-methyl-1-ketotrimethylene)ferrocene (prepared according to Turbitt T. D. and Watts W. E. *J. Organomet. Chem.* 1972, 46, 109-117), 0.214 g (1×10⁻³ mol) of 4,4'-dihydroxybenzophenone, 0.564 g (0.326 cm³, 3.000× 10⁻³ mol) of TiCl₄, 0.384 g (5.862×10⁻³ mol) of zinc powder, 0.472 g (0.482 cm³, 6.000×10⁻³ mol) of anhydrous pyridine and 14+5 cm³ of anhydrous THF.

Compound 11 was isolated as a yellow powder with a 5.9% yield by flash chromatography on silica gel (80 ml, eluting with n-pentane-diethyl ether 3:1) followed with a second chromatography on silica gel (50 ml, eluting with n-pentane-diethyl ether 3:1).

1.8. Mixture of Isomers E and Z of 1,1'-[1-[(4-hydroxyphenyl)(phenyl)-methylidene]trimethylene]ferrocene (12)

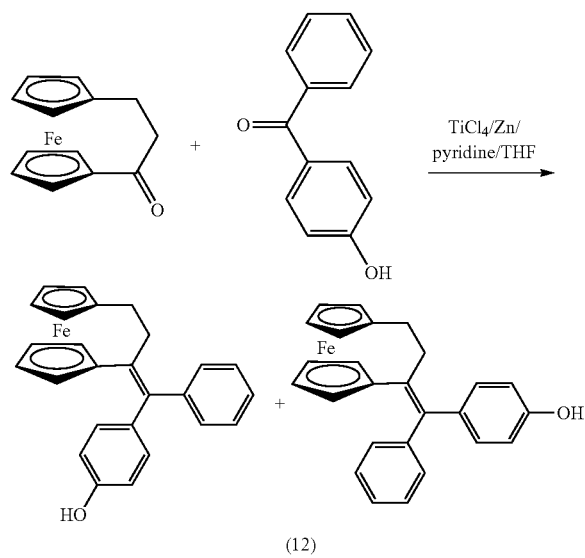

(12)

Compound 12 was prepared according to the procedure described for Compound 4 starting from [3]ferrocenophan-1-one (0.192 g, 0.80 mmol), 4-hydroxybenzophenene (0.158 g, 0.80 mmol), TiCl₄ (0.451 g, 0.261 cm³, 2.4 mmol), zinc powder (0.307 g, 4.694 mmol), anhydrous pyridine (0.379 g, 0.386 cm³, 4.791 mmol) and 10+3 cm³ of anhydrous THF.

Compound 12 was isolated as a yellow powder by flash chromatography on silica gel (80 ml, eluting with n-pentane-diethyl ether 35:15) followed with a second chromatography on silica gel (100 ml, eluting with n-pentane-diethyl ether 3:1).

The compound 12 was finally recrystallized from a mixture of 10 mL of ethyl acetate and 80 mL of n-pentane to yield a mixture of the two isomers in a 1:4.4 ratio.

$^1$H NMR (300.13 MHz, acetone-$d_6$): 8.32 and 8.13 (s, OH); 7.39-7.29 (m, 2H, Ph); 7.28-7.23 (m, 2H, Ph); 7.10-7.01 (m, 1H, Ph); 6.87-6.82 (m, 2H, Ar); 6.57-6.52 (m, 2H, Ar); 4.25 (t, J=1.9 Hz, 2H, Cp); 4.01 and 3.95 (t, J=1.9 Hz, 2H, Cp); 3.98 (t, J=1.9 Hz, 2H, Cp); 3.93 (t, J=1.9 Hz, 2H, Cp); 2.76-2.72 and 2.67-2.64 (m, 2H, CH2); 2.38-2.31 (m, 2H, CH₂)

$^{13}$C NMR (75.48 MHz, acetone-$d_6$): 144.98; 141.57; 135.39; 134.31; 132.35; 131.19; 131.17; 129.98; 128.94; 128.00; 127.35; 114.96; 87.49; 84.52; 71.01; 70.94; 70.92; 69.26; 69.23; 68.87; 68.85; 41.29; 29.16

IR (KBr, cm⁻¹): 2922.9; 2842.1; 1608.3; 1509.2; 1439.2; 1425.9; 1260.9; 1229.2; 1168.9; 1029.3; 830.8; 813.3; 699.6

Analyses: Calculated for $C_{26}H_{22}FeO$: C—76.86%, H—5.46%, found: C—75.71%, H—5.55%

Example 2

Test of Antiproliferative Effects of Compounds of the Invention on Breast and Prostate Cancer Cell Lines The antiproliferative effects of compounds of the invention were tested on MDA-MB-231 cells, which are non-hormone-dependent breast cancer cells, on PC-3 cells, which are non-hormone-dependent prostate cancer cells and on MCF-7 cells, which are hormone-dependent breast cancer cells.

The experimental method used for this test is described in Hillard E. A. et al. *Chem. Med. Chem.* 2006, 1, 551-559.

The results obtained on the MDA-MB-231 and PC-3 cell lines are shown in Table 1 below and demonstrate the antiproliferative properties of the compounds of the invention.

TABLE 1

| | Antiproliferative effect on various cell lines ($IC_{50}$ in µM) | |
|---|---|---|
| Tested compounds | MDA-MB-231 | PC-3 |
| 4 | 0.08 | 0.94 |
| 5 | 0.96 | 1.08 |
| 6 | 2.7 | — |
| 7 | 0.78 | — |
| 8 | 2.7 | — |
| 9 | 0.5 | — |
| 11 | 0.63 | — |
| 12 | 0.47 | — |

— means that the compound of the invention was not tested on the cell line

A comparative study on the MDA-MB-231 line comparing the compounds of the invention and the open compounds showed that the compounds of the invention display a greater cytotoxic activity than the open compounds, as shown in Table 2 below with compounds a and 12.

TABLE 2

| Compound of the invention | Open compound |
| --- | --- |
| 4 (structure, $IC_{50} = 0.08 \cdot 10^{-6}$ M) | (structure, $IC_{50} = 0.5 \cdot 10^{-6}$ M) |
| 12 (structure, $IC_{50} = 0.47 \cdot 10^{-6}$ M) | (structure, $IC_{50} = 1.13 \cdot 10^{-6}$ M) |

Furthermore, on the MCF-7 cell lines (cells containing estrogen receptor alpha ERα), a dual effect is observed for 4. At very low concentration, the estrogen nature of 4, measured without phenol red i.e. in favor of the expression of an estrogen effect, was revealed (the proliferative effect is 162% at $10^{-8}$ M based on the control, as against 264% for estradiol). The purely cytotoxic effect appears at higher concentrations where the resultant of the two components (estrogen effect plus cytotoxic activity) is therefore evidenced. It is thus difficult to achieve very accurate $IC_{50}$ values for the MCF-7 line. However the following values are obtained: approximately $4.10^{-6}$ M for Compound 4 and approximately $10^{-6}$ M for Compound 5.

As a result, Molecule 4 will have, if it is to be used as such, to be dedicated to cancers which do not contain ERα. For cancers containing the receptor ERα, it will thus be necessary to mask the estrogen effect of Compound 4, especially by replacing one of the phenol rings by a phenyl substituted with the chain —O(CH$_2$)$_x$—N(CH$_3$)$_2$ (wherein x=2 to 8 for example).

Also, the presence of two phenol rings on Molecule 4 makes it possible to easily control the lipophilicity of the molecule by substituting one or both OH moieties, thus enhancing its bioavailability.

The invention claimed is:

1. A compound of the following formula (I):

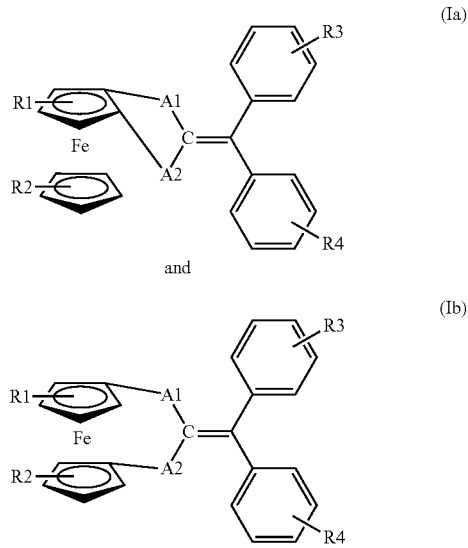

or a pharmaceutically acceptable salt thereof,
wherein:
A1 and A2, independently from each other, are either a bond between the cyclopentadienyl and the carbon of the double bond, or a linear alkyl chain comprising n1 and n2 carbon atoms, respectively, optionally substituted with one or more group(s) selected from halogen; phenyl optionally substituted with OH; (C$_1$-C$_6$)alkyl optionally substituted with one or more halogen(s); and (C$_3$-C$_6$)cycloalkyl optionally substituted with one or more halogen(s),
wherein n1 and n2 are, independently from each other, an integer comprised between 1 and 4,
with the proviso that A1 and A2 are not simultaneously a bond and that the A1-C-A2 chain contains at least 3 carbon atoms,
R1 and R2 each represent hydrogen or together form a linear alkyl chain connecting the two cyclopentadienyl groups and having 3 to 5 carbon atoms, wherein said chain is optionally substituted with one or more group(s) selected from halogen; phenyl optionally substituted with OH; (C$_1$-C$_6$)alkyl optionally substituted with one or more halogen(s); and (C$_3$-C$_6$)cycloalkyl optionally substituted with one or more halogen(s), and
R3 and R4, independently from each other, are hydrogen or a CF$_3$, CN, OR$^5$ or NR$^6$R$^7$ group,
wherein:
R$^5$ is hydrogen or a —CO—(C$_1$-C$_{20}$)alkyl or —(CH$_2$)$_m$NR$^8$R$^9$ group,
R$^6$, R$^7$, R$^8$ and R$^9$ are, independently from one another, hydrogen or a (C$_1$-C$_6$)alkyl or acyl group, and
m is an integer comprised between 2 and 8.

2. The compound according to claim 1, wherein R3 and/or R4 independently from each other, are OR$^5$.

3. The compound according to claim 1, wherein R3 and/or R4 are located in the para-position on the phenyl ring.

4. The compound according to claim 1, wherein R1 and R2 each represent hydrogen.

5. The compound according to claim 1, wherein A1 or A2 represents a bond.

6. The compound according to claim 1 selected from the compounds of the following formulae 4 to 11:

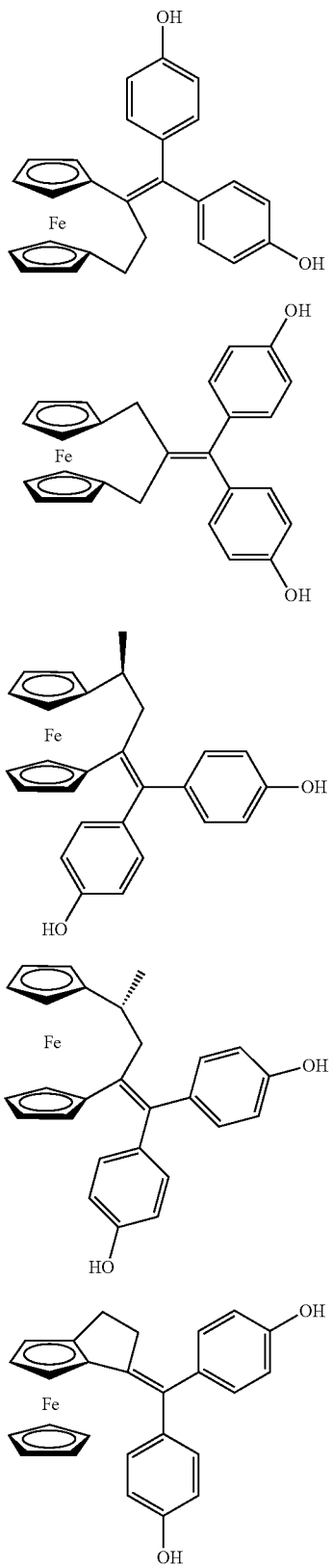

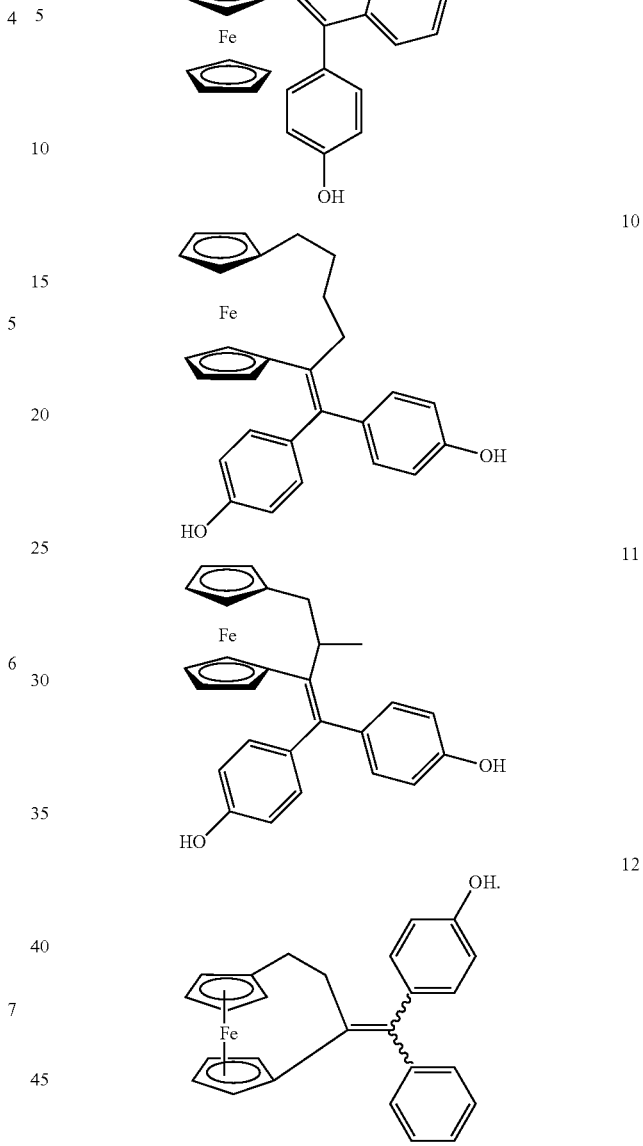

7. A pharmaceutical composition comprising at least one compound according to claim 1, in combination with a pharmaceutically acceptable vehicle.

8. The pharmaceutical composition according to claim 7, further comprising at least one additional active ingredient.

9. A pharmaceutical composition comprising:
(i) at least one compound according to claim 1,
(ii) at least one additional active ingredient,
as combination products to be administered simultaneously, separately or sequentially.

10. The composition according to claim 8, wherein the at least one additional active ingredient is selected from 6-mercaptopurin, fludarabin, cladribin, pentostatin, cytarabin, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethin, cyclophosphamide, ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

11. The composition according to claim 9, wherein the at least one additional active ingredient is selected from 6-mercaptopurine, fludarabin, cladribin, pentostatin, cytarabin, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethin, cyclophosphamide, ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

12. A process for preparing a compound of the formula (Ia) or (Ib) according to claim 1 comprising the following steps:
(i) McMurry coupling of a compound of the following formula (II):

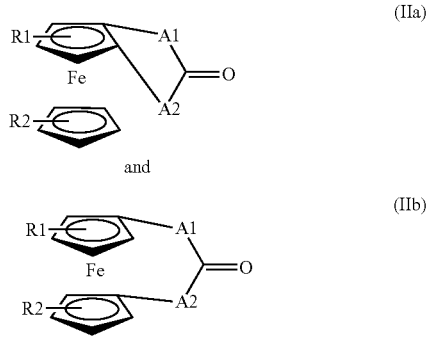

and wherein R1, R2, A1 and A2 are as defined in claim 1, with a compound of the following formula (III):

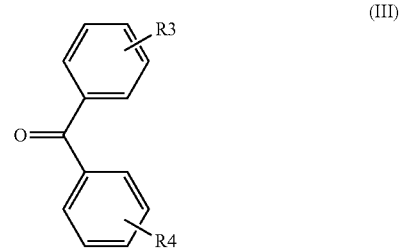

wherein R3 and R4 are as defined in claim 1,
to form the compound of the formula (Ia) or (Ib), and
(ii) recovering the compound of the formula (Ia) or (Ib), obtained in step (i) above.

13. The compound according to claim 1, wherein A1 and A2, independently from each other, are either a bond between the cyclopentadienyl and the carbon of the double bond, or a linear alkyl chain comprising n1 and n2 carbon atoms, respectively, optionally substituted with one or more group(s) selected from halogen; phenyl optionally substituted with OH; $(C_1-C_6)$alkyl optionally substituted with one or more halogen(s); and
$(C_3-C_6)$cycloalkyl optionally substituted with one or more halogen(s),
wherein n1 and n2 are, independently from each other, an integer comprised between 1 and 4, with the proviso that A1 and A2 are not simultaneously a bond and that the A1-C-A2 chain contains 3, 4 or 5 carbon atoms.

14. The compound according to claim 2, wherein R3 and R4 independently from each other, are $OR^5$, wherein $R^5$ is hydrogen or a —CO—$(C_1-C_{20})$alkyl or —$(CH_2)_m NR^8 R^9$ group.

15. The compound according to claim 2, wherein R3 and/or R4 independently from each other, are OH.

16. The compound according to claim 2, wherein R3 and R4 are OH.

17. The compound according to claim 3, wherein R3 and R4 are located in the para-position on the phenyl ring.

* * * * *